(12) United States Patent
Halseth et al.

(10) Patent No.: US 8,852,154 B2
(45) Date of Patent: Oct. 7, 2014

(54) HUBER NEEDLE SAFETY ENCLOSURE

(71) Applicant: C. R. Bard, Inc., Murray Hill, NJ (US)

(72) Inventors: Thor R. Halseth, Ojai, CA (US); John M. Barker, Ventura, CA (US)

(73) Assignee: C. R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 14/070,319

(22) Filed: Nov. 1, 2013

(65) Prior Publication Data
US 2014/0058354 A1 Feb. 27, 2014

Related U.S. Application Data

(63) Continuation of application No. 13/434,368, filed on Mar. 29, 2012, now Pat. No. 8,574,197, which is a continuation of application No. 12/855,605, filed on Aug. 12, 2010, now Pat. No. 8,152,768, which is a continuation of application No. 10/787,605, filed on Feb. 26, 2004, now Pat. No. 7,776,016.

(51) Int. Cl.
*A61M 31/00* (2006.01)
*A61M 5/32* (2006.01)
*A61M 5/158* (2006.01)

(52) U.S. Cl.
CPC ....... *A61M 5/158* (2013.01); *A61M 2005/1581* (2013.01); *A61M 5/3275* (2013.01)
USPC ............ 604/162; 604/192; 604/198; 604/263

(58) Field of Classification Search
USPC ................. 604/162, 192, 198, 263
See application file for complete search history.

(56) References Cited

U.S. PATENT DOCUMENTS

| | | |
|---|---|---|
| 2,847,995 A | 8/1958 | Adams |
| 2,876,770 A | 3/1959 | White |
| 2,925,083 A | 2/1960 | Craig |
| 3,134,380 A | 5/1964 | Armao |
| 3,306,290 A | 2/1967 | Weltman |
| 4,160,450 A | 7/1979 | Doherty |
| 4,235,234 A | 11/1980 | Whitney et al. |
| 4,352,254 A | 10/1982 | Peter et al. |
| 4,352,354 A | 10/1982 | Ujihara |

(Continued)

FOREIGN PATENT DOCUMENTS

| | | |
|---|---|---|
| DE | 3808688 A1 | 1/1989 |
| DE | 3802353 A1 | 8/1989 |

(Continued)

OTHER PUBLICATIONS

EP 03257490 filed Nov. 27, 2003 Office Action dated Aug. 9, 2007.

(Continued)

*Primary Examiner* — Laura Bouchelle
(74) *Attorney, Agent, or Firm* — Rutan & Tucker, LLP

(57) ABSTRACT

A method of using a safety enclosure for a needle, the needle including an aft end and a fore end together forming a right angle, the fore end including a sharp outer end. The method includes providing a safety enclosure including a needle housing and a panel unit, the needle housing having a finger pad, orienting the safety enclosure in a desired location for insertion of the needle, and applying pressure to the finger pad sufficient to cause penetration of the needle at the desired location and to move the panel unit to the installation position.

7 Claims, 5 Drawing Sheets

(56) References Cited

U.S. PATENT DOCUMENTS

| | | |
|---|---|---|
| 4,380,234 A | 4/1983 | Kamen |
| 4,435,175 A | 3/1984 | Friden |
| 4,564,054 A | 1/1986 | Gustavsson |
| 4,592,744 A | 6/1986 | Jagger et al. |
| 4,611,382 A | 9/1986 | Clark |
| 4,615,468 A | 10/1986 | Gay |
| 4,627,842 A | 12/1986 | Katz |
| 4,627,843 A | 12/1986 | Raines |
| 4,631,058 A | 12/1986 | Raines |
| 4,632,671 A | 12/1986 | Dalton |
| 4,645,494 A | 2/1987 | Lee et al. |
| 4,645,495 A | 2/1987 | Vaillancourt |
| 4,655,765 A | 4/1987 | Swift |
| 4,676,783 A | 6/1987 | Jagger et al. |
| 4,710,176 A | 12/1987 | Quick |
| 4,725,267 A | 2/1988 | Vaillancourt |
| 4,760,847 A | 8/1988 | Vaillancourt |
| 4,813,939 A | 3/1989 | Marcus |
| 4,820,282 A | 4/1989 | Hogan |
| D301,742 S | 6/1989 | Wyzgala et al. |
| 4,846,809 A | 7/1989 | Sims |
| 4,867,172 A | 9/1989 | Haber et al. |
| 4,935,011 A | 6/1990 | Hogan |
| 4,935,013 A | 6/1990 | Haber et al. |
| 4,941,881 A | 7/1990 | Masters et al. |
| 4,944,731 A | 7/1990 | Cole |
| 4,950,250 A | 8/1990 | Haber et al. |
| 4,969,876 A | 11/1990 | Patterson |
| 5,013,305 A | 5/1991 | Opie et al. |
| 5,053,017 A | 10/1991 | Chamuel |
| 5,061,250 A | 10/1991 | Shields |
| 5,085,639 A | 2/1992 | Ryan |
| 5,088,982 A | 2/1992 | Ryan |
| 5,092,852 A | 3/1992 | Poling |
| 5,120,320 A | 6/1992 | Fayngold |
| 5,176,653 A | 1/1993 | Metals |
| 5,176,655 A | 1/1993 | McCormick et al. |
| 5,176,662 A | 1/1993 | Bartholomew et al. |
| 5,192,275 A | 3/1993 | Burns |
| 5,295,972 A | 3/1994 | Mischenko |
| 5,312,371 A | 5/1994 | Dombrowski et al. |
| 5,330,438 A | 7/1994 | Gollobin et al. |
| 5,334,158 A | 8/1994 | McLees |
| 5,336,187 A | 8/1994 | Terry et al. |
| 5,350,368 A | 9/1994 | Shields |
| 5,354,281 A | 10/1994 | Chen |
| 5,419,766 A | 5/1995 | Chang et al. |
| 5,433,703 A | 7/1995 | Utterberg et al. |
| 5,451,522 A | 9/1995 | Queener et al. |
| 5,487,728 A | 1/1996 | Vaillancourt |
| 5,487,733 A | 1/1996 | Caizza et al. |
| 5,490,841 A | 2/1996 | Landis |
| 5,505,711 A | 4/1996 | Arakawa et al. |
| 5,520,654 A | 5/1996 | Wahlberg |
| 5,531,704 A | 7/1996 | Knotek |
| 5,531,713 A | 7/1996 | Mastronardi et al. |
| 5,575,773 A | 11/1996 | Song et al. |
| 5,584,813 A | 12/1996 | Livingston et al. |
| 5,584,818 A | 12/1996 | Morrison |
| 5,607,398 A | 3/1997 | Parmigiani |
| 5,637,096 A | 6/1997 | Yoon |
| 5,674,201 A | 10/1997 | Steinman |
| 5,685,860 A | 11/1997 | Chang et al. |
| 5,693,022 A | 12/1997 | Haynes |
| 5,695,474 A | 12/1997 | Daugherty |
| 5,706,520 A | 1/1998 | Thornton et al. |
| 5,755,694 A | 5/1998 | Camus |
| 5,762,632 A | 6/1998 | Whisson |
| 5,779,679 A | 7/1998 | Shaw |
| 5,817,070 A | 10/1998 | Tamaro |
| 5,853,393 A | 12/1998 | Bogert |
| 5,858,004 A | 1/1999 | Shields |
| 5,879,330 A | 3/1999 | Bell |
| 5,885,255 A | 3/1999 | Jaeger, Jr. et al. |
| 5,951,522 A | 9/1999 | Rosato et al. |
| 5,951,525 A | 9/1999 | Thorne et al. |
| 6,042,570 A | 3/2000 | Bell et al. |
| 6,238,375 B1 | 5/2001 | Powell |
| 6,497,669 B1 | 12/2002 | Kensey |
| 6,500,155 B2 | 12/2002 | Sasso |
| 6,537,255 B1 | 3/2003 | Raines |
| 6,613,015 B2 | 9/2003 | Sandstrom et al. |
| 6,623,462 B2 | 9/2003 | Guzzo et al. |
| 6,629,959 B2 | 10/2003 | Kuracina et al. |
| 6,659,984 B2 | 12/2003 | Maclean Crawford et al. |
| 6,663,604 B1 | 12/2003 | Huet |
| 6,676,633 B2 | 1/2004 | Smith et al. |
| 6,689,102 B2 | 2/2004 | Greene |
| 6,699,217 B2 | 3/2004 | Bennett et al. |
| 6,719,727 B2 | 4/2004 | Brimhall et al. |
| 6,749,588 B1 | 6/2004 | Howell et al. |
| 6,755,805 B1 | 6/2004 | Reid |
| 6,783,002 B1 | 8/2004 | Pavlo |
| 6,808,509 B1 | 10/2004 | Davey |
| 6,824,530 B2 | 11/2004 | Wagner et al. |
| 6,911,020 B2 | 6/2005 | Raines |
| 6,918,894 B2 | 7/2005 | Fleury et al. |
| 6,921,388 B2 | 7/2005 | Swenson |
| 6,926,693 B2 | 8/2005 | Enns |
| 6,932,803 B2 | 8/2005 | Newby |
| 6,969,372 B1 | 11/2005 | Halseth |
| 6,972,002 B2 | 12/2005 | Thorne |
| 6,997,902 B2 | 2/2006 | Thorne et al. |
| 7,147,623 B2 | 12/2006 | Mathiasen |
| 7,150,725 B2 | 12/2006 | Wilkinson |
| 7,214,208 B2 | 5/2007 | Vaillancourt et al. |
| 7,361,159 B2 | 4/2008 | Fiser et al. |
| 7,407,493 B2 | 8/2008 | Cane' |
| 7,438,703 B2 | 10/2008 | Barrus et al. |
| 7,601,139 B2 | 10/2009 | Woehr et al. |
| 7,604,616 B2 | 10/2009 | Thoresen et al. |
| 7,637,893 B2 | 12/2009 | Christensen et al. |
| 7,717,888 B2 | 5/2010 | Vaillancourt et al. |
| 7,776,016 B1 | 8/2010 | Halseth et al. |
| 8,066,678 B2 | 11/2011 | Vaillancourt et al. |
| 8,152,768 B2 | 4/2012 | Halseth et al. |
| 8,574,197 B2 | 11/2013 | Halseth et al. |
| 2001/0039401 A1 | 11/2001 | Ferguson et al. |
| 2002/0055711 A1 | 5/2002 | Lavi et al. |
| 2002/0072716 A1 | 6/2002 | Barrus et al. |
| 2002/0099340 A1 | 7/2002 | Crawford et al. |
| 2002/0151852 A1 | 10/2002 | Crawford et al. |
| 2002/0165497 A1 | 11/2002 | Greene |
| 2002/0173749 A1 | 11/2002 | Wagner et al. |
| 2002/0177816 A1 | 11/2002 | Brimhall et al. |
| 2002/0177818 A1 | 11/2002 | Vaillancourt |
| 2002/0183652 A1 | 12/2002 | Kensey |
| 2003/0060774 A1 | 3/2003 | Woehr et al. |
| 2003/0069546 A1 | 4/2003 | Sandstrom et al. |
| 2003/0093101 A1 | 5/2003 | O'Heeron et al. |
| 2003/0105430 A1 | 6/2003 | Lavi et al. |
| 2003/0114797 A1 | 6/2003 | Vaillancourt et al. |
| 2003/0144627 A1 | 7/2003 | Woehr et al. |
| 2003/0181872 A1 | 9/2003 | Newby |
| 2003/0199827 A1 | 10/2003 | Thorne |
| 2004/0044318 A1 | 3/2004 | Fiser et al. |
| 2004/0049159 A1 | 3/2004 | Barrus et al. |
| 2004/0236288 A1 | 11/2004 | Howell et al. |
| 2005/0027263 A1 | 2/2005 | Woehr et al. |
| 2005/0090784 A1 | 4/2005 | Nielsen et al. |
| 2005/0107743 A1 | 5/2005 | Fangrow |
| 2005/0107748 A1 | 5/2005 | Thorne et al. |
| 2005/0107749 A1 | 5/2005 | Smith et al. |
| 2005/0124938 A1 | 6/2005 | Yang |
| 2005/0137528 A1 | 6/2005 | Wilkinson |
| 2006/0064061 A1 | 3/2006 | Solomon et al. |
| 2006/0074387 A1 | 4/2006 | Thorne et al. |
| 2006/0155245 A1 | 7/2006 | Woehr |
| 2006/0161116 A1 | 7/2006 | Willis et al. |
| 2006/0253076 A1 | 11/2006 | Butts et al. |
| 2007/0038182 A1 | 2/2007 | Bialecki et al. |
| 2007/0038183 A1 | 2/2007 | Bialecki et al. |
| 2007/0038184 A1 | 2/2007 | Bialecki et al. |
| 2007/0038185 A1 | 2/2007 | Albert et al. |

(56) References Cited

U.S. PATENT DOCUMENTS

| | | |
|---|---|---|
| 2007/0073221 A1 | 3/2007 | Bialecki et al. |
| 2007/0073222 A1 | 3/2007 | Lilley et al. |
| 2007/0078432 A1 | 4/2007 | Halseth et al. |
| 2008/0147003 A1 | 6/2008 | Menzi et al. |
| 2008/0262434 A1 | 10/2008 | Vaillancourt |
| 2009/0005743 A1 | 1/2009 | Vaillancourt et al. |
| 2009/0143737 A1 | 6/2009 | Kobayashi et al. |
| 2009/0254050 A1 | 10/2009 | Bottcher |
| 2009/0281499 A1 | 11/2009 | Harding et al. |
| 2010/0312183 A1 | 12/2010 | Halseth et al. |
| 2012/0046621 A1 | 2/2012 | Vaillancourt et al. |
| 2012/0065587 A1 | 3/2012 | Barron et al. |
| 2012/0184922 A1 | 7/2012 | Halseth et al. |

FOREIGN PATENT DOCUMENTS

| | | |
|---|---|---|
| DE | 20210394 U1 | 9/2002 |
| EP | 0344606 A2 | 12/1989 |
| EP | 451040 A1 | 10/1991 |
| EP | 0747082 A2 | 12/1996 |
| EP | 0763369 A1 | 3/1997 |
| EP | 1350537 A1 | 10/2003 |
| EP | 1430921 A2 | 6/2004 |
| EP | 2613824 A1 | 7/2013 |
| FR | 2684006 A1 | 5/1993 |
| JP | 61-25558 A | 5/1994 |
| JP | 6226919 A | 8/1994 |
| JP | 7-148270 A | 6/1995 |
| JP | 9099071 A | 4/1997 |
| JP | 2002345955 A | 12/2002 |
| JP | 4355567 | 8/2009 |
| WO | 8807387 A1 | 10/1988 |
| WO | 9400172 A1 | 1/1994 |
| WO | 9806642 | 2/1998 |
| WO | 9959660 A1 | 11/1999 |
| WO | 2005049116 A1 | 6/2005 |
| WO | 2006134100 A1 | 12/2006 |
| WO | 2007094898 A2 | 8/2007 |
| WO | 2012034085 A1 | 3/2012 |

OTHER PUBLICATIONS

EP 03257490 filed Nov. 27, 2003 Search Report dated Jul. 23, 2004.

JP 2003-416415 filed Dec. 15, 2003 Office Action dated Feb. 23, 2007.

JP 2003-416415 filed Dec. 15, 2003 Office Action dated May 30, 2006.

PCT/US11/51102 International Preliminary Report on Patentabillity dated Mar. 21, 2013.

PCT/US11/51102 International Search Report and Written Opinion dated Dec. 23, 2011.

U.S. Appl. No. 10/320,168, filed Dec. 16, 2002 Advisory Action dated Aug. 22, 2005.

U.S. Appl. No. 10/320,168, filed Dec. 16, 2002 Advisory Action dated Nov. 16, 2005.

U.S. Appl. No. 10/320,168, filed Dec. 16, 2002 Final Office Action dated Jul. 13, 2005.

U.S. Appl. No. 10/320,168, filed Dec. 16, 2002 Non-Final Office Action dated Sep. 3, 2004.

U.S. Appl. No. 10/320,168, filed Dec. 16, 2002 Notice of Allowance dated Aug. 29, 2011.

U.S. Appl. No. 10/320,168, filed Dec. 16, 2002 Notice of Allowance dated May 13, 2011.

U.S. Appl. No. 10/787,605, filed Feb. 26, 2004 Advisory Action dated Jul. 16, 2007.

U.S. Appl. No. 10/787,605, filed Feb. 26, 2004 Final Office Action dated Apr. 4, 2008.

U.S. Appl. No. 10/787,605, filed Feb. 26, 2004 Final Office Action dated Jan. 20, 2010.

U.S. Appl. No. 10/787,605, filed Feb. 26, 2004 Final Office Action dated Jan. 25, 2007.

U.S. Appl. No. 10/787,605, filed Feb. 26, 2004 Non-Final Office Action dated Jul. 28, 2006.

U.S. Appl. No. 10/787,605, filed Feb. 26, 2004 Non-Final Office Action dated Oct. 2, 2008.

U.S. Appl. No. 10/787,605, filed Feb. 26, 2004 Non-Final Office Action dated Sep. 10, 2007.

U.S. Appl. No. 11/788,542, filed Apr. 20, 2007 Decision on Appeal dated Oct. 24, 2012.

U.S. Appl. No. 11/788,542, filed Apr. 20, 2007 Examiner's Answer dated Jun. 3, 2010.

U.S. Appl. No. 11/788,542, filed Apr. 20, 2007 Final Office Action dated Dec. 16, 2009.

U.S. Appl. No. 11/788,542, filed Apr. 20, 2007 Non-Final Office Action dated Aug. 27, 2008.

U.S. Appl. No. 11/788,542, filed Apr. 20, 2007 Non-Final Office Action dated Jan. 8, 2009.

U.S. Appl. No. 11/788,542, filed Apr. 20, 2007 Non-Final Office Action dated Jul. 10, 2009.

U.S. Appl. No. 12/221,034, filed Jul. 30, 2008 Final Office Action dated Dec. 8, 2009.

U.S. Appl. No. 12/221,034, filed Jul. 30, 2008 Non-Final Office Action dated Jan. 30, 2009.

U.S. Appl. No. 12/221,034, filed Jul. 30, 2008 Non-Final Office Action dated Jun. 26, 2009.

U.S. Appl. No. 12/221,034, filed Jul. 30, 2008 Notice of Allowance dated Feb. 25, 2010.

U.S. Appl. No. 12/855,605, filed Aug. 12, 2010 Final Office Action dated Oct. 4, 2011.

U.S. Appl. No. 12/855,605, filed Aug. 12, 2010 Non-Final Office Action dated Apr. 27, 2011.

U.S. Appl. No. 12/855,605, filed Aug. 12, 2010 Notice of Allowance dated Dec. 12, 2011.

U.S. Appl. No. 13/285,774, filed Oct. 31, 2011 Non-Final Office Action dated Dec. 13, 2012.

U.S. Appl. No. 13/285,774, filed Oct. 31, 2011 Non-Final Office Action dated Jul. 3, 2012.

U.S. Appl. No. 13/285,774, filed Oct. 31, 2011 Non-Final Office Action dated Jun. 3, 2013.

U.S. Appl. No. 13/434,368, filed Mar. 29, 2012 Non-Final Office Action dated Mar. 20, 2013.

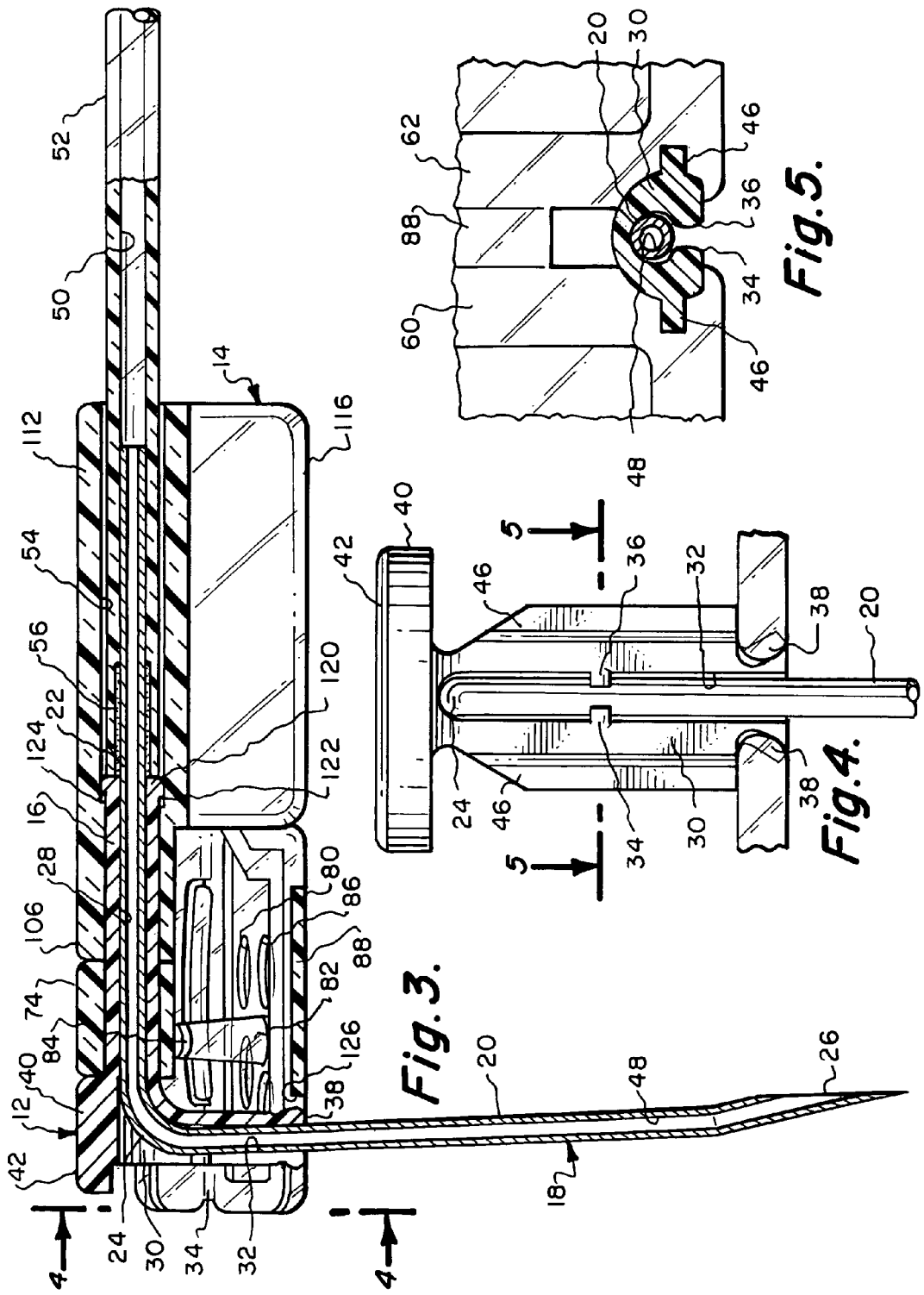

HUBER NEEDLE SAFETY ENCLOSURE

PRIORITY

This application is a continuation of U.S. patent application Ser. No. 13/434,368, filed Mar. 29, 2012, now U.S. Pat. No. 8,574,197, which is a continuation of U.S. patent application Ser. No. 12/855,605, filed Aug. 12, 2010, now U.S. Pat. No. 8,152,768, which is a continuation of U.S. patent application Ser. No. 10/787,605, filed Feb. 26, 2004, now U.S. Pat. No. 7,776,016, each of which is incorporated by reference in its entirety into this application.

FIELD OF THE INVENTION

This invention is directed to a safety enclosure for a hypodermic needle known as a Huber needle and more particularly to improvements over a prior art type of safety enclosure which is defined within U.S. Pat. No. 5,951,522, entitled HYPODERMIC NEEDLE SAFETY ENCLOSURE, issued Sep. 14, 1999, and which is incorporated by reference in its entirety into this application.

DESCRIPTION OF THE RELATED ART

Within the medical field, some patients require the use of a vascular access device as part of his or her care. A vascular access device is used on a patient to provide pain drugs, chemotherapy, antibiotics, antiviral or antifungal drugs as well as for hydration and nutrition. In recent years, there has been a substantial increase in the number of patients with implanted ports. An implanted port requires a special needle to be inserted through the skin of the patient and into the port. The most common type of such a needle includes a ninety degree bend and is commonly referred to as a Huber needle. Because of this ninety degree bend configuration of the needle, removing the needle at the end of the infusion therapy is particularly dangerous to the medical practitioner. This danger has to do with applying an outward force to the needle, and when the needle is exterior of the port, there is a natural bounce-back of the needle. It is during this bounce-back that a needlestick injury would be common to the medical practitioner. As a result, the medical practitioner may be subjected to the same infection that the patient is subjected to.

Huber needles are commonly used for long term infusion therapy. The angle relationship of the needle allows the aft end of the needle to be safely anchored by being taped to the exterior surface of the skin of the patient in the area surrounding the infusion port. The Huber needle is commonly left in place for several days and possibly weeks. It is common that the aft end of the Huber needle has attached thereto "wings" with these "wings" to be placed against the patient's skin and then by taping of these "wings" to the patient's skin thereby fixes in place the needle relative to the patient.

Implanted ports have advantages, such as reduced risk of infection, no need for a dressing, no need to restrict activities of the patient permitting the patient to normalize his or hers life. However, the implanted port has one significant disadvantage and that there is a high degree of needlestick injury during removal of the Huber needle by the practitioner. It is well known that there are hundreds of thousands of needlestick injuries in the medical field each and every year within the United States alone. Not only does the needlestick injury subject the medical practitioner to viruses and bacteria but also to AIDS, hepatitis and other serious diseases. In the past, a needlestick injury has been attributed to carelessness on the part of the medical practitioner. In actuality, carelessness has little to do with needlestick injuries as it is directly related to the difficulty of removing the needle.

Inherently, the procedure of removing of a Huber needle results in bounce-back which comprises a rebounding effect. Bounce back is an action which by pulling on the needle or needle attachment, the sharpened end of the needle hooks into the port. This hooking of the needle is due to a snag occurring impeding the removal of the needle from the septum. The medical practitioner thus pulls harder contracting the muscles of his or her arm. When the needle is finally released, the muscles relax and an opposite movement takes place and drives the Huber needle point down into the non-dominant hand of the medical practitioner thus causing the common form of needlestick injury.

In the past, there have been devices that have been marketed to help reduce the risk of needlestick injury. The most significant of these devices is what is shown and described in U.S. Pat. No. 5,591,522, which has been previously mentioned. This patent covers a product that is being manufactured and sold throughout the world. The subject matter of the present invention is directed to improvements in the product of this patent with the resultingly improved product to be manufactured and sold by the assignee that has been manufacturing and selling the product of this prior patent.

There are certain deficiencies in the product of this prior patent. The prior product had a tendency to move to the safety position inadvertently, like when a patient would roll over on his or her side. This is not desirable as the needle is automatically withdrawn from the port. The gripping handle within the prior product was freely pivotable relative to the needle. This caused a certain amount of instability making it difficult for the medical practitioner to manipulate and install the needle. Also, the needle would have a tendency to rock longitudinally in position and eventually would withdraw itself from the access site. Ergonomically, the housing of the prior art product did not have any finger pads that facilitated the location of the medical practitioner's fingers that would assist in installing the needle. The panel unit within the prior art product did not have a smooth surface that would be in contact with the patient's skin which had a tendency to be uncomfortable to the patient. Also, there was no ventilation structure within the prior art product which would tend to eliminate sweating by the patient in the area of the installed enclosure. The locking device for locking the panel together, when in the safety position, was located at the exterior edge of the panel assembly which had a tendency to bend and thereby not function as desired. It is also possible for the Huber needle in the prior art product to move longitudinally relative to the panel unit or wings. It is definitely desirable that the panel unit (wings) be longitudinally fixed in position relative to the needle. There was no structure in the prior art product that assisted in retaining the needle in position relative to the panel unit (wings) during assembly. The prior art product also had several different adhesive joints and it would be desirable to decrease the number of these adhesive joints which would lower manufacturing expense.

SUMMARY OF THE INVENTION

The first basic embodiment of the present invention is directed to a Huber needle that is mounted within a needle housing. This needle housing has a through passage and a slot that extends at a right angle from the through passage. The Huber needle is mounted in both the through passage and the slot. A panel unit is composed of a series of edge interconnected sheet material planar panels assembled in an enclosing arrangement defining an enclosed area. Each of the panels are hingedly movable to a pair of the panels. The panel unit is movable between an installation position where the sharp outer end of the needle projects from the panel unit and a safety position where the sharp outer end is covered by the panels.

A further embodiment of the present invention is where the first basic embodiment is modified by the needle housing having an annular collar with this annular collar to longitudinally restrain the needle housing relative to the panel unit.

A further embodiment of the present invention is where the first basic embodiment is modified by the panel unit and the needle housing cooperating to have a locking device to be engaged only when the panel unit is in the installation position.

A further embodiment of the present invention is where the just previous embodiment is modified by the locking device being defined as a notch formed in the panel unit and an outwardly flared collar formed on the needle housing.

A further embodiment of the present invention is where the first basic embodiment is modified by the slot in the needle housing having at least one ridge which is to function to produce an interference fit in conjunction with the Huber needle.

A further embodiment of the present invention is where the first basic embodiment is modified by the needle housing including an enlarged finger pad with the enlarged finger pad to provide a flat surface facilitating application of manual pressure that is necessary to install the Huber needle and also for practitioner comfort.

A further embodiment of the present invention is where the first basic embodiment is modified by including a gripping handle fixed to one of the panels with this gripping handle to be usable during installing of the enclosure.

A further embodiment of the present invention is where the just previous embodiment is modified by having the handle extend to a lower position which is to rest on the skin of the patient to prevent rocking movement of the needle when installed in the port.

A further embodiment of the present invention is where the first basic embodiment is modified by the panel unit having side edges when in the installation position with each side edge of the side edges including an elongated protuberance which functions as a guide to assist the user as to where squeezing manual pressure is to be applied to move the panel unit from the installation position to the safety position.

A further embodiment of the present invention is where the first basic embodiment is modified by the panel unit including wing finger pads to indicate to the user where manual pressure may be applied to facilitate correct installation of the Huber needle within an implanted port.

A further embodiment of the present invention is where the first basic embodiment is modified by the planar panels are defined as having flat exterior surfaces that are to be in contact with the skin of the patient on which the enclosure is mounted for reason of comfort to the patient.

A further embodiment of the present invention is where the just previous embodiment is modified by the flat exterior surfaces each having a series of ventilation holes.

A further embodiment of the present invention is where the first basic embodiment is modified by there being included at least one post mounted on one of the panels and located within the enclosed area and the posts including a locking means with this locking means to lockingly engage with another of the panels to maintain the panel unit in the safety position once the panel unit is moved to the safety position.

A further embodiment of the present invention is where the first basic embodiment is modified by having the Huber needle adhesively attached to an extension tube with this extension tube being mounted coaxially with the needle housing.

A second basic embodiment of the present invention is directed to a Huber needle mounted within a needle housing and the Huber needle having a sharp outer end. A panel unit is composed of a series of edge connected sheet material planar panels assembled in an enclosing arrangement defining an enclosed area. Each of the handles are hingedly movable to a pair of the panels. The panel unit is movable between an installation position where the sharp outer end projects from the unit and a safety position where the sharp outer end is covered by the panels. A gripping handle is fixed to one of the panels with the gripping handle to be utilized during installing of the enclosure in the installation position.

A further embodiment of the present invention is where the second basic embodiment is modified by the panel unit having side edges when in the installation position with each side edge of the side edges including an elongated protuberance which functions as a guide to assist the user as to where squeezing manual pressure is to be applied to move the panel unit from the installation position to the safety position.

A further embodiment of the present invention is where the second basic embodiment is modified by a pair of the planar panels are defined as having flat exterior surfaces that are to be in contact with the skin of the patient on which the enclosure is mounted.

A further embodiment of the present invention is where the just previous embodiment is modified by the flat exterior surfaces each having a series of ventilation holes.

A further embodiment of the present invention is where the second basic embodiment is modified by there being included at least one post mounted on one of the panels and located within the enclosed area with this post including a locking means and this locking means to lockingly engage with another of the panels to maintain the panel unit in the safety position once the panel is moved to the safety position.

A further embodiment of the present invention is where the second basic embodiment is modified by having the gripping handle extend to a lower position which is to rest on the skin of the patient and prevent rocking movement of the needle.

A third basic embodiment of the present invention is directed to a Huber needle safety enclosure which has a Huber needle mounted within a needle housing with this Huber needle having a sharp outer end. A panel unit is composed of a series of edge connected sheet material panels assembled in an enclosing arrangement defining an enclosed area with each of the panels being hingedly movable to a pair of the panels. The panel unit is movable between a installation position where the sharp outer end projects from the panel unit and a safety position where the sharp outer end is covered by the panels. The panel unit has side edges when in the installation position with each side edge including an elongated protuberance which functions as a guide to assist the user as to where squeezing manual pressure is to be applied to move the panel unit from the installation position to the safety position.

A further embodiment of the present invention is directed to an improvement of the third basic embodiment by the panel unit including wing finger pads to indicate to the user where manual pressure is to be applied to facilitate correct installation of the Huber needle.

A further embodiment of the present invention is directed to an improvement of the third basic embodiment by a pair of the planar panels having flat exterior surfaces that are to be in contact with the skin of the patient on which the enclosure is mounted.

A further embodiment of the present invention is directed to an improvement of the just previous embodiment by the flat exterior surfaces each having a series of ventilation holes.

A further embodiment of the present invention is directed to an improvement of the third basic embodiment by there being included at least one post mounted on one of the panels and located within an enclosed area with the post including a locking means and this locking means to lock and engage with another of the panels to maintain the panel unit in the safety position once the panel is moved to the safety position.

A fourth basic embodiment of Huber needle safety enclosure of this invention is defined as comprising a Huber needle mounted within a needle housing with the Huber needle having a sharp outer end. A panel unit is composed of a series of edge connected sheet material planar panels assembled in an enclosing arrangement defining an enclosed area. Each of the panels are hingedly movable to a pair of the panels. The panel unit is moved between an installation position where the sharp outer end projects from the panel unit and a safety position where the sharp outer end is covered by the panels. At least one post is mounted on the panels and located within an enclosed area. The post includes a locking means with the locking means to lockingly engage with another of the panels to maintain the panel unit in the safety position once the panel is moved to the safety position.

A further embodiment of the present invention is where the fourth basic embodiment is modified by there being a plurality of the posts with at least two in number of the posts being mounted on different panels.

A further embodiment of the present invention is where the fourth basic embodiment is modified by the locking means being defined as a hook with this hook to engage with an aperture formed in a panel.

BRIEF DESCRIPTION OF THE DRAWINGS

For a better understanding of the present invention, reference is to be made to the accompanying drawings. It is to be understood that the present invention is not limited to the precise arrangement shown in the drawings.

FIG. 3 is a longitudinal cross-sectional view through the enclosure of the present invention taken along line 3-3 of FIG. 2;

FIG. 4 is a front end view of the enclosure of the present invention taken along line 4-4 of FIG. 3;

FIG. 5 is a transverse cross-sectional view through the needle housing utilized in conjunction with the enclosure of the present invention taken along line 5-5 of FIG. 4;

DETAILED DESCRIPTION OF THE INVENTION

Figure 1:
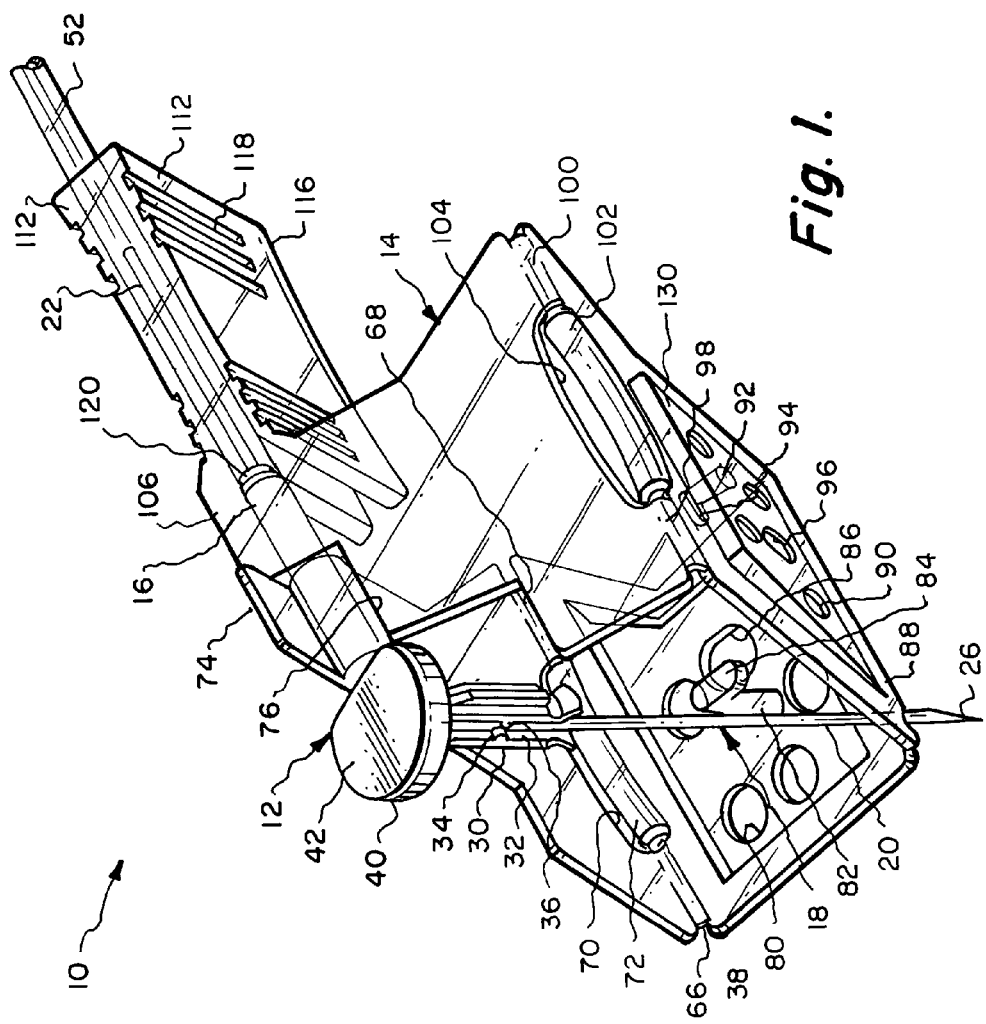
FIG. 1 is a frontal isometric view of the Huber needle safety enclosure of the present invention showing the enclosure in an intermediate position between an installing position and the safety position with the sharpened point of the needle partially extended from the panel unit of the enclosure.

Referring particularly to the drawings, there is shown the Huber needle safety enclosure 10 of this invention. The safety enclosure 10 includes, generally, a needle housing 12 and a panel unit 14. The needle housing 12 includes an elongated cylindrical hinge tube 16 which is constructed of plastic as well as almost all of the components of this enclosure 10. The only part that is not constructed of plastic will be the Huber needle 18 itself, which will be constructed of metal.

The Huber needle 18 is in the shape of a right angle and has a fore end 20 and an aft end 22. The fore end 20 is connected to the aft end 22 at a bend 24. The free end of the fore end 20 is formed into a sharpened tip 26. The hinge tube 16 has a through passage 28. The aft end 22 of the Huber needle 18 is located in a close fitting but yet slidable manner within the through passage 28. Integrally connected to the hinge tube 16 at 20 its front end is a sleeve 30. Longitudinally formed within the sleeve 30 is a slot 32. The wall surface of the slot 32 includes a pair of ridges 34 and 36. The ridges 34 and 36 are located in lateral alignment with each other. However, this is not mandatory as they could be slightly spaced apart. The fore end 20 of the Huber needle 18 is press fitted within the slot 32 with the ridges 34 and 36 forming a tight or an interference fit that tends to hold the Huber needle 18 in conjunction with the slot 32. This holding of the Huber needle 18 in position with the slot 32 is generally during assembly of the safety enclosure 10 and will tend to prevent accidental dislodgement of the Huber needle 18 from the slot 32. The reason for this is that the safety enclosure 10 is manufactured at a plurality of different stations at an assembly line. One of the first steps in the assembly line is to insert the Huber needle 18 in conjunction with the needle housing 12 and then that resultingly assembled unit is then moved to the next station. The reason for the ridges 34 and 36 is to prevent the needle 18 from accidentally disengaging from the needle housing 12 during movement from one station to another. The outer end of the sleeve 30 is formed into an outwardly flared collar 38. The function of this collar 38 will be explained further on in the specification.

Figure 2:
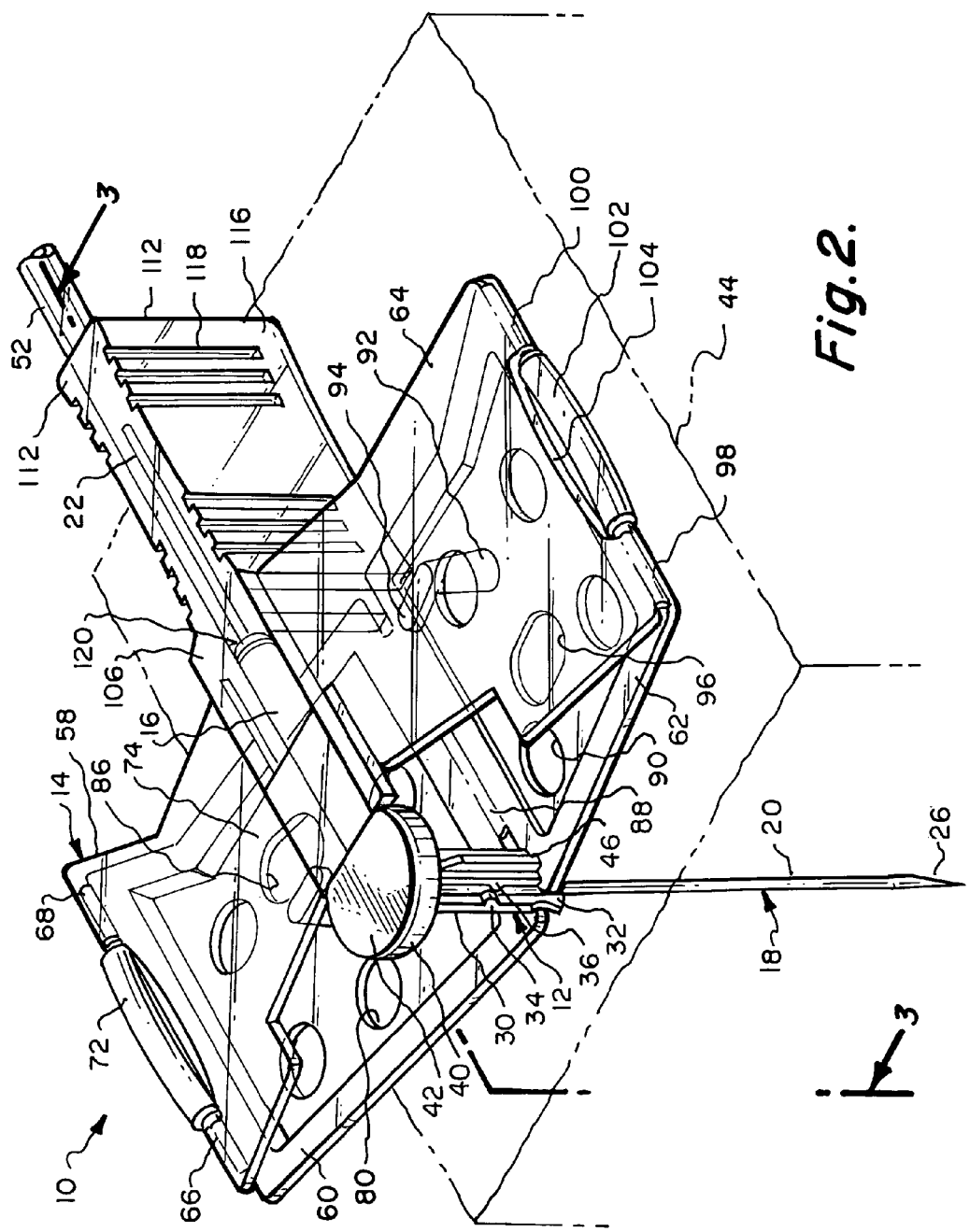
FIG. 2 is a frontal isometric view showing the enclosure in the installed position and depicting installation within a port implanted within a body of a human.

The needle housing 12 includes an enlarged finger pad 40 which has a flat top 42. The flat top 42 is to facilitate the application of finger pressure by the installer of the enclosure 10 of this invention. Applying finger pressure onto flat top 42 will cause the sharpened tip 26 and the fore end 20 to penetrate a septum of an implanted port, which is not shown. However, the implanted port would be included within the human body 44, which is depicted generally in FIG. 2. The enlarged finger pad 40 is formed integral to the sleeve 30 and also to the hinge tube 16. Formed diametrically opposite the exterior surface of the sleeve 30 are a pair of elongated ridges 46. The function of these ridges will also be explained further on in the specification. The Huber needle 18 has a through conduit 48. This conduit 48 connects to a through passage 50 formed within an extension tube 52. Generally, the extension tube 52 will be made of plastic. The extension tube 52 is placed coaxially with bore 54 of the hinge tube 16. Bore 54 is of a slightly greater diameter than the through passage 28. It is to be understood that fluids, which includes drugs, solutions, hydrating liquids, etc., are to be supplied through the through passage 50 to within the through conduit 48 to be dispensed exteriorly of the sharpened tip 26. It is also considered to be within the scope of this invention that fluid could be withdrawn from the through conduit 48 and the through passage 50 for the purpose of performing medical tests or for other medical reasons. In order to insure that the extension tube 52 remains in position, there will be an adhesive 56 that will be applied which will adhesively secure the extension tube 52 to the aft end 22 of the Huber needle 18. Any desirable medically approved adhesive will be satisfactory.

The panel unit 14 is constructed of an end panel 58, an intermediate panel 60, another intermediate panel 62 and another end panel 64. All of the panels 58, 60, 62 and 64 are generally constructed planar sheet material with plastic being preferred. Panel 58 is connected to panel 60 by living hinge sections 66 and 68. Formed within the end panel 58 is a cutout area 70. Integrally mounted on the edge of the panel 60 is an elongated protuberance 72. The elongated protuberance 72 passes within the cutout area 70 as end panel 58 pivots relative to intermediate panel 60 about living hinges 66 and 68. The free outer edge of the end panel 58 is formed into flat extension 74. Integrally connected to the lower surface of flat extension 74 is a tube 76. Tube 76 has a through passage 78.

Formed through the surface of the intermediate panel 60 are a series of ventilation holes 80. Also, fixedly mounted on the inside surface of the intermediate panel 60 is a post 82. The upper end of the post 82 is formed into a lateral extension, which is defined as a hook 84. Alongside of the post 82 and formed within the panel 60 is an elongated hole 86. There are shown four in number of the ventilation holes 80 formed within the intermediate panel 60. However, it is considered to be within the scope of this invention that the number of ventilation holes 80 could be increased or decreased without departing from the scope of this invention.

The intermediate panel 60 is connected by a living hinge 88 to intermediate panel 62. It is to be understood that a living hinge is a term that is commonly used to define a thin or narrowed piece of plastic that connects between two thicker pieces of plastic with that thin piece of plastic allowing pivoting movement between the pieces of plastic. The intermediate panel 62 also includes a plurality of ventilation holes 90 with four in number being shown with it again being understood that this number could be increased or decreased without departing from the scope of this invention. Also mounted on the inside surface of the intermediate panel 62 is a post 92. The upper end of the post 92 terminates in a laterally extending member defined as a hook 94. Mounted directly adjacent the post 90 is elongated hole 96. The elongated hole 96 extends entirely through the intermediate panel 62.

The intermediate panel 62 is connected by living hinges 98 and 100 to end panel 64. In between the living hinges 98 and 100 there is located an elongated protuberance 102 which is fixedly mounted on the intermediate panel 62. The elongated protuberance 102 is positioned within cutout area 104 which is formed within the end panel 64. The free side edge of the end panel 64 is formed into a flat extension 106. Fixedly mounted to the underside of the flat extension 106 is a tube 108. Formed through the tube 108 is a through passage 110. The diameter of the through passage 110 equals the diameter of the through passage 78. Fixedly attached to the flat extension 106 and also to tube 108 is a gripping handle 112. The bore 54 is formed through the 20 gripping handle 112. Gripping handle 112 has a lower extension 116. The sidewalls of the gripping handle 112 include a series of elongated grooves 118.

The manufacturing procedure for the safety enclosure 10 of this invention is as follows: The aft end of the Huber needle 18 is inserted within the through passage 28 of the hinge tube 16. The fore end 20 is moved until it fully engages with slot 32 with the ridges 34 and 36 creating a binding action against the fore end 20. The panel unit 14 is positioned so tube 76 abuts tube 108 and through passages 78 and 110 align. At this time, the enlarged collar is then forced through the passages 78 and 110. It is to be noted that the enlarged collar 120 has a beveled forward surface and a vertical rear wall 122. The hinge tube 16 is moved sufficiently through the passages 78 and 110 until the rear wall 122 and collar 120 are located within the bore 54. At this time, withdrawal of the hinge tube 16 is prevented by the rear wall 122 which is not capable of being conducted over annular wall 124 of the tube 108.

Formed between the intermediate panels 60 and 62 is a notch 126. The panels 60 and 62 are moved to the position shown in FIG. 2 until outwardly flared collar 38 engages with the notch 126. This, in essence, provides a slight lock to hold the panel unit 14 in the position shown in FIG. 2 so end panel 58 forms a relatively sharp acute angle relative to intermediate panel 60. At this particular time, the hook 84 abuts against the inside surface of the end panel 58. At the same time, the end panel 64 forms an acute angle with intermediate panel 62 with hook 94 to abut against the inside surface of end panel 64. In order to protect the assembler by being stuck by the sharpened end 26 of the Huber needle 18, there is placed over the fore end 20 a protective tube 128. The now assembled safety enclosure 10 is to be placed within a shipping container, irradiated or gassed in order to sterilize the enclosure 10, and then transport such to the consumer.

The consumer removes the safety enclosure 10 from its package, which will generally occur in close proximity to the human body 44. A medical practitioner will then remove the protective tube 128 from the Huber needle 18. The medical practitioner would grab the gripping handle 112 between thumb and middle finger and orient the safety enclosure 10 in the proper position for insertion. That position would be with the sharpened end 26 directly against the septum of the implant port, which is not shown, which is mounted within the human body 44. The medical practitioner then places his or her index or first finger on flat top 42 or against flat extension 74 and 106. The medical practitioner then applies a downward pressure sufficient to cause the sharpened end 26 to penetrate the implant port. The implant port will be covered with a flexible rubber layer which is to be penetrated by the fore end 20 of the Huber needle 18. Once the fore end 20 is inserted to the proper depth within the implant port, the exterior surface of the intermediate panels 60 and 62 is to be located against the human body 44. In order to aid comfort to the patient, not only is there provided the ventilation holes 80 and 90 but there is also provided a flattened area 130 on the exterior surface of intermediate panel 62. There is a similar flattened area, which is not shown, on the exterior surface of the intermediate panel 60. These flattened areas, when against the body of the patient, provide a more comfortable surface than if the surfaces were not flat.

One advantage of the structure of the safety enclosure 10 of the present invention is that when it is installed in conjunction with the human body 44 that the lower extension 116 of the gripping handle 112 actually rests on the body of the human 44. This resting of the lower extension 116 essentially prevents any rocking movement of the safety enclosure 10 relative to the implant port. Rocking motion can occur during normal daily activity, which includes sleeping of the patient. This rocking motion over a period of time can actually cause the Huber needle 18 to be withdrawn from the implant port.

The locking action produced by outwardly flared collar 38 being engaged with the notch 126 can be overcome by the application of a small amount of force in the form of a squeezing action that is applied to the elongated protuberances 72 and 102. These protuberances 72 and 102, because of their shape relative to the side edges of the end panels 58 and 64 and intermediate panels 60 and 62, provides a smoothly contoured structure that readily indicates to the user that the hand is in the proper position for applying the squeezing force. It is to be remembered that the overall structure of the present invention is quite small with the distance between the protuberances 72 and 102, in the position shown in FIG. 2, being approximately one and one-quarter inches. Because the medical practitioner installer is working with such a small unit, the using of the smoothly contoured protuberances 72 and 102 grant to the medical practitioner a certain feel that tells that medical practitioner that the hand is in the proper position for applying the squeezing force.

Figure 6:
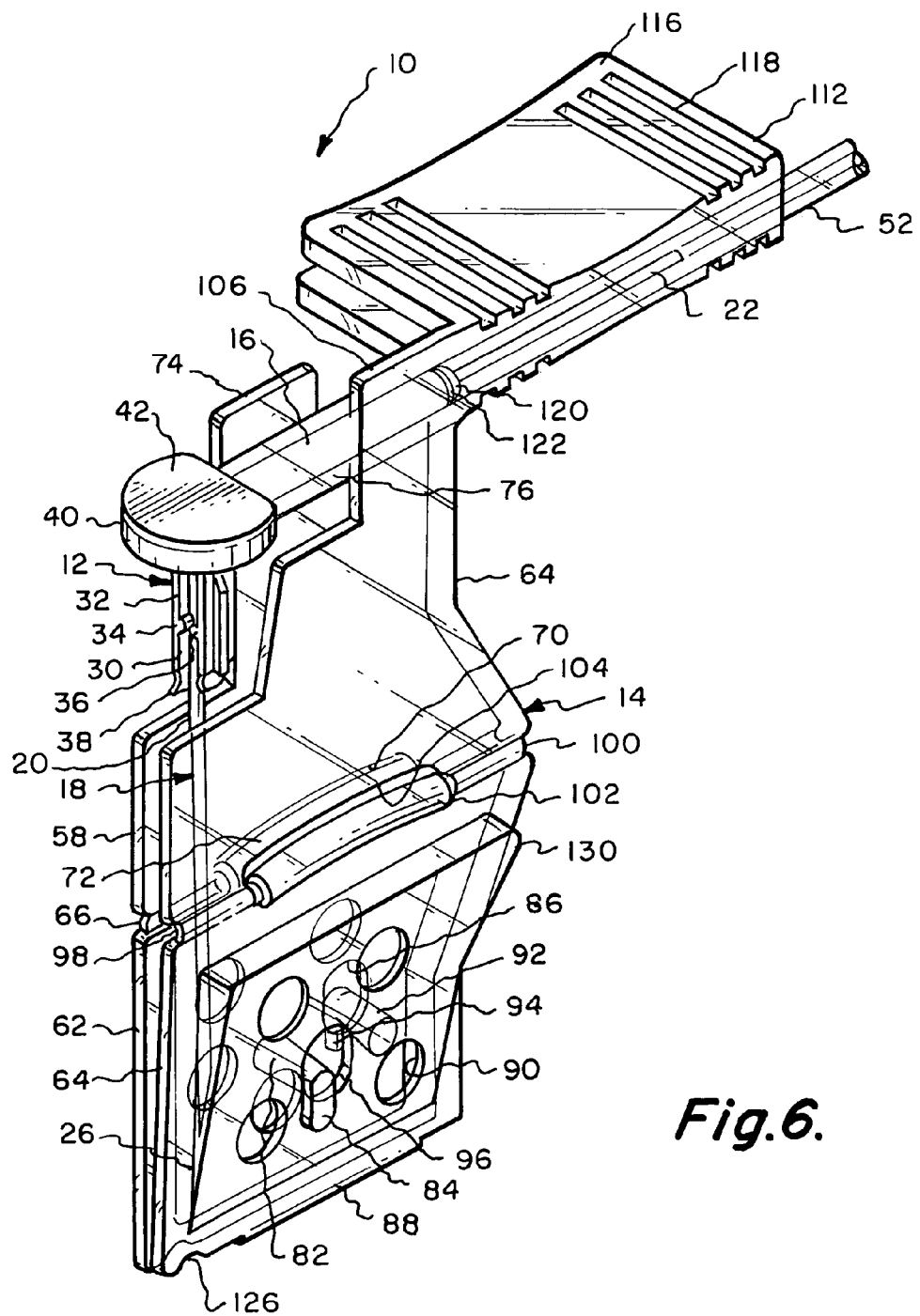
FIG. 6 is a front isometric view of the enclosure showing the enclosure in the safety position.
Figure 7:
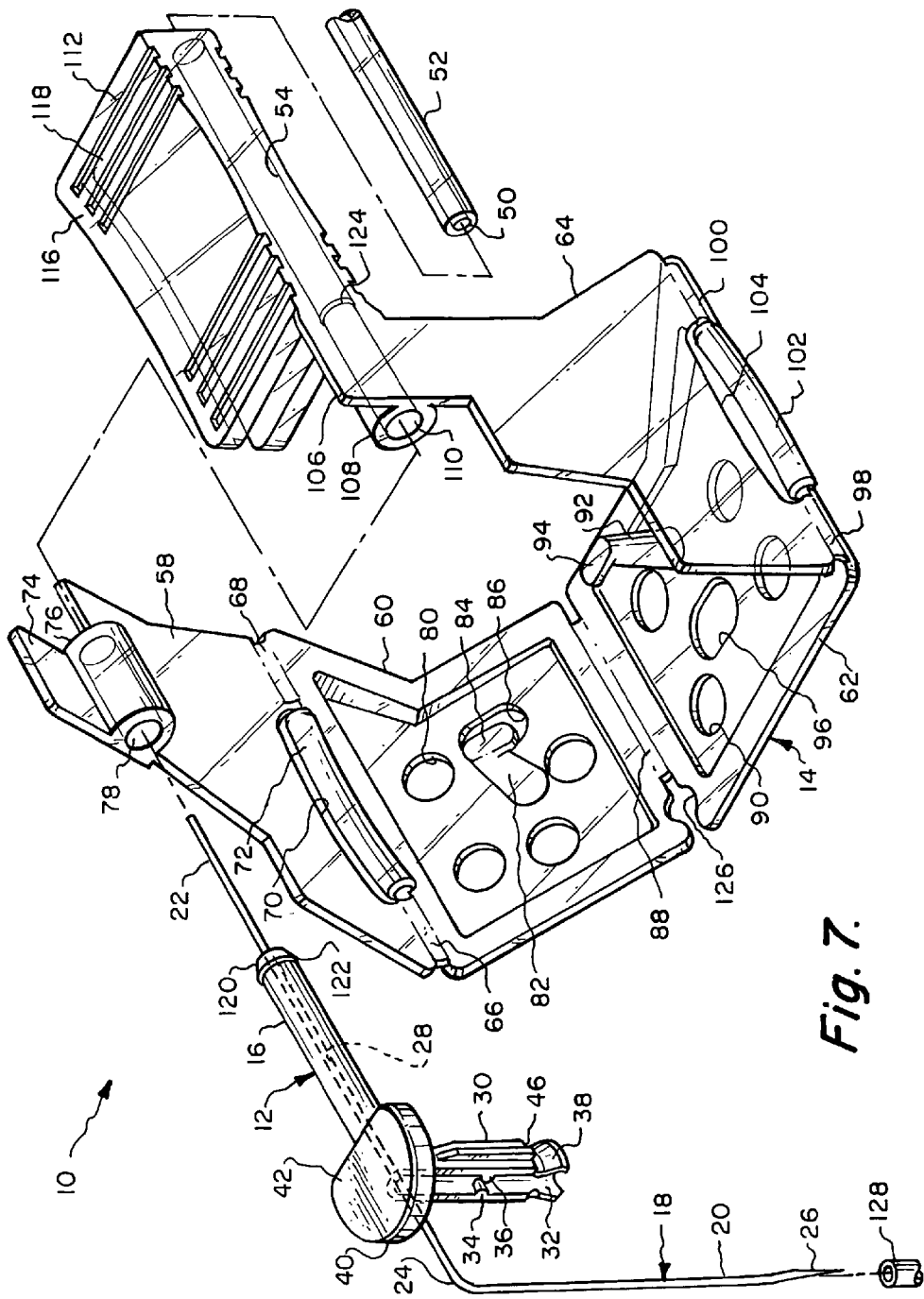
FIG. 7 is an exploded frontal isometric view of the Huber needle safety enclosure of the present invention.

Let it be assumed that it is now desired for the medical practitioner to remove the safety enclosure 10 of this invention from the implant port. The safety enclosure 10, shown in FIG. 2, will actually be taped with adhesive tape, which is not shown, to the human body 44. A dressing would then be applied. This tape is removed. The medical practitioner places a thumb on elongated protuberance 102 and an index finger on elongated protuberance 72 and applies a squeezing force. Only a small amount of force is required that will cause the end panels 58 and 64 to move upwardly disengaging the collar 38 from the notch 126. Further squeezing force results in the end panel 58 to be moved alongside of end panel 64. At the same time, intermediate panel 60 is moved directly alongside of intermediate panel 62. In this position, the hook 84 is conducted through the elongated hole 96 with the undersurface of the hook 84 abutting against the exterior surface of the intermediate panel 62. At the same time, the hook 94 is conducted through the elongated hole 86 with the undersurface of the hook 94 being located against the exterior surface of the intermediate panel 60. The result is that the safety enclosure 10 is in the position shown in FIG. 6 and is locked in that position by the hooks 84 and 94. The sharpened end 26 of the Huber needle 18 is clamped between the intermediate panels 60 and 62 making it impossible for the medical practitioner to experience any needlestick injury. At this particular time, the safety enclosure 10 is then discarded at an appropriate discarding location.

The including of the grooves 118 on the gripping handle 112 is to provide a roughened surface to facilitate gripping of the gripping handle 112. Also, it is to be noted that the exterior sidewalls of the gripping handle 112 are formed slightly concave, which again are for the purpose of ergonomics to make it more comfortable when using of the gripping handle 112. The flattened areas, such as flattened area 130, permit the application of a cushioning pad, if such is desired. This cushioning pad would be positioned between the safety enclosure and the skin of the patient.

The structure of this invention can be incorporated within different sizes of Huber needles 18. The hinge tube 16 could be manufactured in different colors with a particular color to be coordinated with a particular size of Huber needle 18. Also, the panel unit 14 could be manufactured of a transparent plastic material to allow visibility of the access site of the Huber needle 18 within the implant port by the medical practitioner. Typically, the length and gauge of the fore end 20 of the Huber needle 18 might possibly be printed on the exterior surface of the end panels 58 and 64 as there will probably be utilized different lengths for the fore end 20 of the Huber needle 18.

The discussion included in this patent is intended to serve as a basic description. The reader should be aware that the specific discussion may not explicitly describe all embodiments possible and alternatives are implicit. Also, this discussion may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. It should also be understood that a variety of changes may be made without departing from the essence of the invention. Such changes are also implicitly included in the description. These changes still fall within the scope of this invention.

Further, each of the various elements of the invention and claims may also be achieved in a variety of manners. This disclosure should be understood to encompass each such variation, be it a variation of any apparatus embodiment. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. It should be understood that all actions may be expressed as a means for taking that action or as an element which causes that action. Similarly, each physical element disclosed should be understood to encompass a disclosure of the action which that physical element facilitates. Such changes and alternative terms are to be understood to be explicitly included in the description.

What is claimed is:

1. A method of using a safety enclosure for a needle, the needle including an aft end and a fore end together forming a right angle, the fore end including a sharp outer end, the method comprising:
   providing a safety enclosure including:
      a needle housing including a finger pad with a flat surface generally perpendicular to a longitudinal axis of the needle fore end and generally parallel to a longitudinal axis of the needle aft end in both an installation position and a safety position, the finger pad operational in the installation position; and
      a panel unit including a series of planar panels assembled in an enclosing, arrangement defining an enclosed area, the panel unit movable between the installation position where the needle sharp outer end projects from the panel unit and a safety enclosure safety position where the needle sharp outer end is covered by the panels;
   orienting the safety enclosure in a desired location for insertion of the needle; and
   applying pressure to the finger pad sufficient to cause penetration of the needle at the desired location and to move the panel unit to the installation position.

2. The method according to claim 1, wherein the needle housing further comprises an outwardly flared collar that engages a notch in the panel unit in the installation position to releasably lock the panel unit.

3. The method according to claim 1, further comprising a gripping handle to assist in the orienting step, wherein the gripping handle rests on the skin of the patient in the installation position and prevents longitudinal rocking movement of the needle.

4. The method according to claim 1, wherein the panel unit comprises side edges including elongated protuberances, the method further comprising transitioning the safety enclosure from the installation position to the safety position by pressing the elongated protuberances toward one another.

5. The method according to claim 4, wherein the panel unit comprises a first panel including a first locking means, and a second panel including a second locking means, wherein the transitioning comprises conducting the first locking means through an opening in the second panel and conducting the second locking means through an opening in the first panel.

6. The method according to claim 1, further comprising arranging adhesive tape over at least a portion of the panel unit at the desired location following, the applying step.

7. The method according to claim 6, further comprising removing the tape prior to transitioning the safety enclosure from the installation position to the safety position.

\* \* \* \* \*